United States Patent [19]

Baker

[11] Patent Number: 6,147,036
[45] Date of Patent: Nov. 14, 2000

[54] PROCESS FOR PREPARING COMPOSITIONS USEFUL AS INTERMEDIATES FOR PREPARING LUBRICATING OIL AND FUEL ADDITIVES AND DERIVATIVES THEREOF

[75] Inventor: Mark R. Baker, Lyndhurst, Ohio

[73] Assignee: The Lubrizol Corporation, Wickliffe, Ohio

[21] Appl. No.: 09/043,402

[22] PCT Filed: Aug. 8, 1997

[86] PCT No.: PCT/US97/14028

§ 371 Date: Mar. 23, 1998

§ 102(e) Date: Mar. 23, 1998

[87] PCT Pub. No.: WO98/05741

PCT Pub. Date: Feb. 12, 1998

Related U.S. Application Data

[63] Continuation-in-part of application No. 08/694,139, Aug. 8, 1996, Pat. No. 5,779,742.

[51] Int. Cl.$^7$ ................................................. C10M 133/16
[52] U.S. Cl. .................. 508/454; 508/452; 508/500; 508/551; 508/555; 560/179; 560/183; 564/201; 564/204
[58] Field of Search ..................... 508/426, 551, 508/452, 305, 454, 500, 555; 44/330; 564/201, 204; 560/179, 183

[56] References Cited

U.S. PATENT DOCUMENTS

| | | |
|---|---|---|
| Re. 26,433 | 8/1968 | LeSuer . |
| 3,259,578 | 7/1966 | Dickson et al. . |
| 3,269,946 | 8/1966 | Wiese . |
| 3,271,310 | 9/1966 | LeSuer . |
| 3,306,908 | 2/1967 | LeSuer . |
| 4,512,903 | 4/1985 | Schlicht et al. . |
| 4,525,541 | 6/1985 | Kitahara et al. ................ 525/337 |
| 4,654,435 | 3/1987 | Kitahara et al. ................ 560/61 |
| 5,696,060 | 12/1997 | Baker ................ 508/222 |
| 5,696,067 | 12/1997 | Adams ................ 508/476 |
| 5,739,356 | 4/1998 | Dietz et al. ................ 549/285 |
| 5,779,742 | 7/1998 | Baker ................ 508/222 |
| 5,786,490 | 7/1998 | Dietz ................ 508/246 |
| 5,840,920 | 11/1998 | Baker ................ 549/266 |
| 5,851,377 | 12/1998 | Bush ................ 208/48 AA |
| 5,851,966 | 12/1998 | Baker et al. ................ 508/452 |
| 5,856,279 | 1/1999 | Baker ................ 508/222 |

FOREIGN PATENT DOCUMENTS

| | | |
|---|---|---|
| 0 759 443 | 2/1997 | European Pat. Off. . |
| 0 759 444 | 2/1997 | European Pat. Off. . |
| 0 882 745 | 12/1998 | European Pat. Off. . |
| 2 103 686 | 8/1972 | Germany . |

*Primary Examiner*—Margaret Medley
*Attorney, Agent, or Firm*—Joseph P. Fischer; David M. Shold

[57] ABSTRACT

A process for reacting certain carboxylic reactants with olefinic compounds then reacting the intermediate prepared thereby with ammonia, a hydrazine or an amine, and/or a reactive metal or reactive metal compound, products prepared thereby and, additive concentrates and lubricating oil and fuel compositions.

15 Claims, No Drawings

PROCESS FOR PREPARING COMPOSITIONS USEFUL AS INTERMEDIATES FOR PREPARING LUBRICATING OIL AND FUEL ADDITIVES AND DERIVATIVES THEREOF

CROSS REFERENCE TO RELATED APPLICATIONS

This application is a continuation-in-part of application Ser. No. 08/694,139 filed Aug. 8, 1996, now U.S. Pat. No. 5,779,742, which is hereby incorporated herein by reference.

FIELD OF THE INVENTION

This invention relates to a process for preparing compositions which are useful as intermediates for the preparation of low chlorine containing additives for lubricating oils and normally liquid fuels, compounds prepared by the process, and derivatives thereof.

BACKGROUND OF THE INVENTION

Numerous types of additives are used to improve lubricating oil and fuel compositions. Such additives include, but are certainly not limited to dispersants and detergents of the ashless and ash-containing variety, oxidation inhibitors, anti-wear additives, friction modifiers, and the like. Such materials are well known in the art and are described in many publications, for example, Smalheer, et al, "Lubricant Additives", Lezius-Hiles Co., Cleveland, Ohio, U.S.A. (1967); M. W. Ranney, Ed., "Lubricant Additives", Noyes Data Corp., Park Ridge, N.J., U.S.A. (1973); M. J. Satriana, Ed., "Synthetic Oils and Lubricant Additives, Advances since 1977", Noyes Data Corp., Park Ridge N.J., U.S.A. (1982), W. C. Gergel, "Lubricant Additive Chemistry", Publication 694-320-65R1 of the Lubrizol Corp., Wickliffe, Ohio, U.S.A. (1994); and W. C. Gergel et al, "Lubrication Theory and Practice" Publication 794-320-59R3 of the Lubrizol Corp., Wickliffe, Ohio, U.S.A. (1994); and in numerous United States patents, for example Chamberlin, III, U.S. Pat. No. 4,326,972, Schroeck et al, U.S. Pat. No. 4,904,401, Blystone et al., U.S. Pat. No. 5,356,546 and Ripple et al, U.S. Pat. No. 4,981,602. Many such additives are frequently derived from carboxylic reactants, for example, acids, esters, anhydrides, lactones, and others. Specific examples of commonly used carboxylic compounds used as intermediates for preparing lubricating oil additives include alkyl- and alkenyl substituted succinic acids and anhydrides, polyolefin substituted carboxylic acids, aromatic acids, such as salicylic acids, and others. Illustrative carboxylic compounds are described in Meinhardt, et al, U.S. Pat. No. 4,234,435; Norman et al, U.S. Pat. No. 3,172,872; LeSuer et al, U.S. Pat. No. 3,454,607, and Rense, U.S. Pat. No. 3,215,707.

Many carboxylic intermediates used in the preparation of lubricating oil additives contain chlorine. While the amount of chlorine present is often only a very small amount of the total weight of the intermediate, the chlorine frequently is carried over into the carboxylic derivative which is desired as an additive. For a variety of reasons, including environmental reasons, government regulation, and commercial reasons the industry has been making efforts to reduce or to eliminate chlorine from additives designed for use as lubricant or fuel additives. The matter of chlorine content in additives is discussed in numerous patents including U.S. Pat. Nos. 5,356,552; 5,370,805; 5,445,657 and 5,454,964.

Accordingly, it is desirable to provide low chlorine or chlorine free additives and intermediates useful for preparing them for use in lubricants and fuels.

The present invention provides an improved process and products prepared by the improved process and derivatives which meet these requirements.

B. B. Snider and J. W. van Straten, J. Org. Chem., 44, 3567–3571 (1979) describe certain products prepared by the reaction of methyl glyoxylate with several butenes and cyclohexenes. K. Mikami and M. Shimizu, Chem. Rev., 92, 1021–1050 (1992) describe carbonyl-ene reactions, including glyoxylate-ene reactions. D. Savostianov (communicated by P. Pascal), C.R. Acad. Sc. Paris, 263, (605–7) (1966) relates to preparation of some α-hydroxylactones via the action of glyoxylic acid on olefins. M. Kerfanto et. al., C.R. Acad. Sc. Paris, 264, (232–5) (1967) relates to condensation reactions of α-α-di-(N-morpholino)-acetic acid and glyoxylic acid with olefins. B. B. Jarvis et al, Synthesis, 1079–82 (1990) relates to reactions of oxocarboxylic acids with olefins under acidic conditions to give α-hydroxy butyrolactones.

Fuels containing additives to improve the performance thereof are described in numerous patents including the following United States patents:

| | |
|---|---|
| 4,071,327 | 5,336,278 |
| 4,379,065 | 5,356,546 |
| 4,400,178 | 5,458,793 |
| 4,564,460 | |

SUMMARY OF THE INVENTION

The present invention provides a process comprising reacting, optionally in the presence of an acidic catalyst selected from the group consisting of organic sulfonic acids, heteropolyacids, Lewis acids, and mineral acids, (A) at least one olefinic compound containing at least one group of the formula (I)

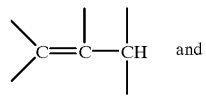

and (B) at least one carboxylic reactant selected from the group consisting of compounds of the formula (V)

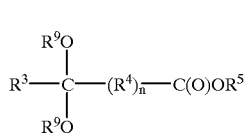

wherein each of $R^3$, $R^5$ and one $R^9$ is independently H or a hydrocarbyl group and the other $R^9$ is a hydrocarbyl group, $R^4$ is a divalent hydrocarbylene group, and n is 0 or 1, in amounts ranging from 0.6 moles (B) per mole of (A) to 3 moles (B) per equivalent of (A).

Products prepared by the process and derivatives thereof, e.g., with amines, basic metal compounds, alcohols, etc., are also contemplated.

Also provided are additive concentrates for preparing lubricating oil and fuel compositions, lubricating oil compositions and fuel compositions.

DETAILED DESCRIPTION OF THE PREFERRED EMBODIMENTS

As used herein, the terms "hydrocarbon", "hydrocarbyl" or "hydrocarbon based" mean that the group being described has predominantly hydrocarbon character within the context of this invention. These include groups that are purely hydrocarbon in nature, that is, they contain only carbon and hydrogen. They may also include groups containing non-hydrocarbon atom containing substituents or atoms which do not alter the predominantly hydrocarbon character of the group. Such substituents may include halo-, alkoxy-, nitro-, etc. These groups also may contain hetero atoms. Suitable hetero atoms will be apparent to those skilled in the art and include, for example, sulfur, nitrogen and oxygen. Therefore, while remaining predominantly hydrocarbon in character within the context of this invention, these groups may contain atoms other than carbon present in a chain or ring otherwise composed of carbon atoms.

In general, no more than about three non-hydrocarbon substituents or hetero atoms, and preferably no more than one, will be present for every 10 carbon atoms in the hydrocarbon, hydrocarbyl or hydrocarbon based groups. Most preferably, the groups are purely hydrocarbon in nature, that is they are essentially free of atoms other than carbon and hydrogen.

Throughout the specification and claims the expression soluble or dispersible is used. By soluble or dispersible is meant that an amount needed to provide the desired level of activity or performance can be incorporated by being dissolved, dispersed or suspended in an oil of lubricating viscosity or in a normally liquid fuel. Usually, this means that at least about 0.001% by weight of the material can be incorporated in a lubricating oil or normally liquid fuel. For a further discussion of the terms oil soluble and dispersible, particularly "stably dispersible", see U.S. Pat. No. 4,320,019 which is expressly incorporated herein by reference for relevant teachings in this regard.

As noted hereinabove, provided by this invention is a process for preparing low chlorine or chlorine free compositions useful as low chlorine or chlorine free additives and intermediates for preparing such additives for lubricating oil and fuel compositions.

The Process

In one embodiment, the present invention relates to a process comprising reacting, optionally in the presence of an acidic catalyst selected from the group consisting of organic sulfonic acids, heteropolyacids, Lewis acids, and mineral acids, (A) at least one olefinic compound containing at least one group of the formula

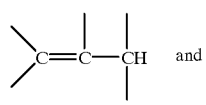

(I)

and (B) at least one carboxylic reactant selected from the group consisting of compounds of the formula (V)

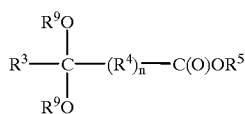

wherein each of $R^3$, $R^5$ and one $R^9$ is independently H or a hydrocarbyl group and the other $R^9$ is a hydrocarbyl group, $R^4$ is a divalent hydrocarbylene group, and n is 0 or 1, in amounts ranging from 0.6 moles (B) per mole of (A) to 3 moles (B) per equivalent of (A).

Reactants (A) and (B) may be present at the outset of the reaction. Under these conditions, all of (A) and (B) may be present at the same time; however, it has been found that improvements in yield and purity of the product arising from the reaction of (A) and (B) are often attained when the carboxylic reactant (B) is added to the olefinic compound (A) either portionwise or continuously over an extended period of time, usually up to about 10 hours, more often from 1 hour up to about 6 hours, frequently from about 2 to about 4 hours.

Optionally the process may be conducted in the presence of a solvent. Well known solvents include aromatic and aliphatic solvents, oil, etc. When a solvent is used, the mode of combining reactants does not appear to have any effect.

The process may be conducted in the presence of an azeotroping solvent. Well known azeotroping solvents include toluene, xylene, cyclohexane, etc. Cyclohexane is preferred.

Reactant (B) can be mixed with the olefinic compound all at once as in a batch reaction or can be added dropwise or metered into a reactor over a period of time. Compared to glyoxylic acid and homologs thereof the acetals, ketals, hemiacetals, and hemiketals, and especially the esters, are more miscible with the olefinic compound owing to the lower polarity thereof compared to a carboxylic acid such as glyoxylic acid. Furthermore, the absence of water in the carboxylic reactant (B) makes mixing with the olefinic compound easier than mixing of glyoxylic and the olefinic compound. However, it is still important to insure good mixing especially in large scale synthesis.

The Catalyst

The process of this invention is optionally conducted in the presence of an acidic catalyst. Acid catalysts, such as organic sulfonic acids, for example, paratoluene sulfonic acid, methane sulfonic acid and sulfonated polymers such as those marketed under the tradename Amberlyst® (Rohm & Haas), heteropolyacids, the complex acids of heavy metals (e.g., Mo, W, Sn, V, Zr, etc.) with phosphoric acids (e.g., phosphomolybdic acid), and mineral acids, for example, $H_2SO_4$ and phosphoric acid, are useful. The amount of catalyst used is generally small, ranging from about 0.01 mole % to about 10 mole %, more often from about 0.1 mole % to about 2 mole %, based on moles of olefinic reactant.

(A) The Olefinic Compound

The olefinic compound employed as a reactant in the process of this invention contains at least one group of the formula

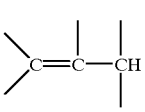

(I)

and has the general formula $(R^1)(R^2)C=C(R^6)(CH(R^7)(R^8))$ (III)

wherein each of $R^1$ and $R^2$ is, independently, hydrogen or a hydrocarbon based group. Each of $R^6$, $R^7$ and $R^8$ is, independently, hydrogen or a hydrocarbon based group; preferably at least one is a hydrocarbon based group containing at least 7 carbon atoms. These olefinic compounds are diverse in nature.

Virtually any compound containing an olefinic bond may be used provided it meets the general requirements set forth hereinabove for (III) and does not contain any functional groups (e.g., primary or secondary amines) that would interfere with the carboxylic reactant (B). Useful olefinic compounds may be terminal olefins, i.e., olefins having a $H_2C=C$ group, or internal olefins. Useful olefinic compounds may have more than one olefinic bond, i.e., they may be dienes, trienes, etc. Most often they are mono-olefinic. Examples include linear -olefins, cis- or trans- disubstituted olefins, trisubstituted olefins and tetrasubstituted olefins.

When (A) is a monoolefinic, one mole of (A) contains one equivalent of C=C; when (A) is diolefinic, one mole of (A) contains 2 equivalents of C=C bonds; when (A) is triolefinic, one mole of (A) contains 3 equivalents of C=C bonds, and so forth.

Aromatic double bonds are not considered to be olefinic double bonds within the context of this invention.

As used herein, the expression "polyolefin" defines a polymer derived from olefins. The expression "polyolefinic" refers to a compound containing more than one C=C bond.

Among useful compounds are those that are purely hydrocarbon, i.e., those substantially free of non-hydrocarbon groups or atoms, or they may contain one or more non-hydrocarbon groups or atoms as discussed in greater detail herein.

In one embodiment, the olefinic compounds are substantially hydrocarbon, that is, each R group in (III) is H or contains essentially carbon and hydrogen. In one aspect within this embodiment, each of $R^1$, $R^2$, $R^7$ and $R^8$ is hydrogen and $R^6$ is a hydrocarbyl group containing from 7 to about 5,000 carbon atoms, more often from about 30 up to about 200 carbon atoms, preferably from about 50 up to about 100 carbon atoms. In another aspect of this embodiment, each of $R^1$ and $R^2$ is hydrogen, $R^6$ is H or a lower alkyl group, especially methyl, and the group (CH$(R^7)(R^8)$) is a hydrocarbyl group containing from 7 to about 5,000 carbon atoms, more typically from about 30 up to about 200 carbon atom, preferably from 50 up to about 100 carbon atoms.

As used here, and throughout the specification and claims, the expression "lower" with "alkyl", "alkenyl", etc. means groups having 7 or fewer carbon atoms, for example, methyl, ethyl and all isomers of propyl, butyl, pentyl, hexyl and heptyl, ethylene, butylene, etc.

In another embodiment, one or more of the R groups present in (III) is an organic radical which is not purely hydrocarbon. Such groups may contain or may be groups such as carboxylic acid, ester, amide, salt, including ammonium, amine and metal salts, cyano, hydroxy, thiol, tertiary amino, nitro, alkali metal mercapto and the like. Illustrative of olefinic compounds (III) containing such groups are methyl oleate, oleic acid, 2-dodecenedioic acid, octene diol, linoleic acid and esters thereof, and the like.

Preferably, the hydrocarbyl groups are aliphatic groups. In one preferred embodiment, when an R group is an aliphatic group containing a total of from about 30 to about 100 carbon atoms, the olefinic compound is derived from homopolymerized and interpolymerized $C_{2-18}$ mono- and di-olefins, preferably 1-olefins. In a preferred embodiment, the olefins contain from 2 to about 5 carbon atoms, preferably 3 or 4 carbon atoms. Examples of such olefins are ethylene, propylene, butene-1, isobutylene, butadiene, isoprene, 1-hexene, 1-octene, etc. R groups can, however, be derived from other sources, such as monomeric high molecular weight alkenes (e.g. 1-tetracontene), aliphatic petroleum fractions, particularly paraffin waxes and cracked analogs thereof, white oils, synthetic alkenes such as those produced by the Ziegler-Natta process (e.g., poly-(ethylene) greases) and other sources known to those skilled in the art. Any unsaturation in the R groups may be reduced by hydrogenation according to procedures known in the art, provided at least one olefinic group remains as described for (III).

In one preferred embodiment, at least one R is derived from polybutene, that is, polymers of $C_4$ olefins, including 1-butene, 2-butene and isobutylene. Those derived from isobutylene, i.e., polyisobutylenes, are especially preferred. In another preferred embodiment, R is derived from polypropylene. In another preferred embodiment, R is derived from ethylene-alpha olefin polymers, including ethylene-α-olefin-diene polymers, especially those wherein the diene is a non-conjugated diene. Representative of such polymers are the ethylene-propylene copolymers and ethylene-propylene-diene terpolymers marketed under the Trilene® tradename by the Uniroyal Company. Molecular weights of such polymers may vary over a wide range, but especially preferred are those having number average molecular weights ($\overline{M}_n$) ranging from about 300 up to 20,000, preferably about 700 to about 10,000, often from about 900 to about 2,500. In one preferred embodiment, the olefin is an ethylene-propylene-diene terpolymer having $\overline{M}_n$ ranging from about 900 to about 8,000, often up to about 2,000. Such materials are included among the Trilene® polymers marketed by the Uniroyal Company, Middlebury, Conn., U.S.A. Also contemplated are polydiene polymers, those prepared by polymerizing dienes.

Ethylene-alpha olefin copolymers and ethylene-lower olefin-diene terpolymers are described in numerous patent documents, including European patent publication EP 279, 863, Japanese patent publication 87-129,303 and the following United States patents:

| | |
|---|---|
| 3,598,738 | 4,357,250 |
| 4,026,809 | 4,658,078 |
| 4,032,700 | 4,668,834 |
| 4,137,185 | 4,937,299 |
| 4,156,061 | 5,324,800 |
| 4,320,019 | | each of which is incorporated herein by reference for relevant disclosures of these ethylene based polymers A preferred source of hydrocarbyl groups R are polybutenes obtained by polymerization of a $C_4$ refinery stream having a butene content of 35 to 75 weight percent and isobutylene content of 15 to 60 weight percent in the presence of a Lewis acid catalyst such as aluminum trichloride or boron trifluoride. These polybutenes contain predominantly (greater than 80% of total repeating units) isobutylene repeating units of the configuration

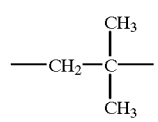

These polybutenes are typically monoolefinic, that is they contain but one olefinic bond per molecule.

The olefinic compound may be a polyolefin comprising a mixture of isomers wherein from about 50 percent to about 65 percent are tri-substituted olefins wherein one substituent contains from 2 to about 500 carbon atoms, often from about 30 to about 200 carbon atoms, more often from about 50 to about 100 carbon atoms, usually aliphatic carbon atoms, and the other two substituents are lower alkyl.

When the olefin is a tri-substituted olefin, it frequently comprises a mixture of cis- and trans- 1-lower alkyl, 1-(aliphatic hydrocarbyl containing from 30 to about 100 carbon atoms), 2-lower alkyl ethene and 1,1-di-lower alkyl, 2-(aliphatic hydrocarbyl containing from 30 to about 100 carbon atoms) ethene.

In one embodiment, the monoolefinic groups are predominantly vinylidene groups, i.e., groups of the formula

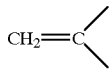

especially those of the formula

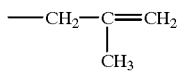

although the polybutenes may also comprise other olefinic configurations.

In one embodiment the polybutene is substantially monoolefinic, comprising at least about 30 mole %, preferably at least about 50 mole % vinylidene groups, more often at least about 70 mole % vinylidene groups. Such materials and methods for preparing them are described in U.S. Pat. Nos. 5,071,919; 5,137,978; 5,137,980; 5,286,823 and 5,408, 018, and in published European patent application EP 646103-A1, each of which is expressly incorporated herein by reference. They are commercially available, for example under the tradenames Ultravis (BP Chemicals) and Glissopal (BASF).

In one embodiment, the olefinic compound is a polyolefin comprising a mixture of isomers, at least about 50% by weight of the mixture comprising isomers of the formula $$H_2C=C(R^6)(CH(R^7)(R^8))$$

wherein $R^6$ is H or lower alkyl, preferably methyl.

As is apparent from the foregoing, olefins of a wide variety of type and of molecular weight are useful for preparing the compositions of this invention. Useful olefins are usually substantially hydrocarbon and have number average molecular weight ranging from about 100 to about 70,000, more often from about 200 to about 7,000, even more often from about 1,300 to about 5,000, frequently from about 400 to about 3,000. Lower olefins such as those containing from about 7 to about 30 carbon atoms, for example, octenes, octadecenes, mixed olefin, such as $C_{8-28}$ linear olefins, are useful. Linear alpha-olefins containing from 7–100 carbon atoms, preferably from 8–50 carbons and offer from 8 to about 28 carbon atoms are useful.

Specific characterization of olefin reactants (A) used in the processes of this invention can be accomplished by using techniques known to those skilled in the art. These techniques include general qualitative analysis by infrared and determinations of average molecular weight, e.g., $\overline{M}_n$, number average molecular weight, and $\overline{M}_w$, weight average molecular weight, etc. employing vapor phase osmometry (VPO) and gel permeation chromatography (GPC).

Viscosity average molecular weights ($\overline{M}v$) have widely been used in polymer chemistry as approximations of weight average molecular weights. The value of $\overline{M}v$ is close to that of $\overline{M}w$. The magnitude of the three average molecular weights are:

$$\overline{M}w>\overline{M}v>\overline{M}n$$

$\overline{M}v$ is calculated from intrinsic viscosity.

Intrinsic viscosity is a physical constant of a polymer. It is the measure of the ability of a polymer to increase the viscosity of a solvent when the polymer is dissolved in the solvent. The viscosity of the solution is markedly greater than that of the solvent. This is one of the striking properties which high molecular weight compounds possess. Intrinsic viscosity is a thickening coefficient of a polymer in solution.

Structural details can be elucidated employing proton and carbon 13 ($C^{13}$) nuclear magnetic resonance (NMR) techniques. NMR is useful for determining substitution characteristics about olefinic bonds, and provides some details regarding the nature of the substituents. More specific details regarding substituents about the olefinic bonds can be obtained by cleaving the substituents from the olefin by, for example, ozonolysis, then analyzing the cleaved products, also by NMR, GPC, VPO, and by infra-red analysis and other techniques known to the skilled person.

(B) The Carboxylic Reactant

The carboxylic reactant is at least one member selected from the group consisting of compounds of the formula

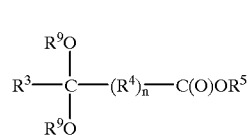

(V)

wherein each of $R^3$, and one $R^9$ is independently H or a hydrocarbyl group and the other $R^9$ is a hydrocarbyl group.

$R^3$ is usually H or an aliphatic group, that is, alkyl or alkenyl, preferably alkyl, more preferably lower alkyl. Especially preferred is where $R^3$ is H or methyl, most preferably, H.

$R^4$ is a divalent hydrocarbylene group. This group may be aliphatic or aromatic, but is usually aliphatic. Often, $R^4$ is an alkylene group containing from 1 to about 3 carbon atoms. The 'n' is 0 or 1; that is, in one embodiment $R^4$ is present and in another embodiment, $R^4$ is absent. More often, $R^4$ is absent.

When $R^5$ is hydrocarbyl, it is usually an aliphatic group, often a group containing from 1 to about 30 carbon atoms, often from 8 to about 18 carbon atoms. In another embodiment, $R^5$ is lower alkyl, wherein "lower alkyl" is defined hereinabove. Most often, $R^5$ is H or lower alkyl, especially methyl, ethyl, propyl and butyl.

One $R^9$ is H or hydrocarbyl, preferably H or alkyl, preferably lower alkyl, especially methyl, ethyl, propyl and butyl. The other $R^9$ is preferably lower alkyl, most preferably methyl, ethyl, propyl or butyl.

Examples of carboxylic reactants (B) are the hemiacetals and hemiketals of omega-oxoalkanoic acids such as glyoxylic acid and keto alkanoic acids such as pyruvic acid, levulinic acid, ketovaleric acids, and ketobutyric acids, and the corresponding acetals and ketals, and numerous others. The skilled worker, having the disclosure before him, will readily recognize the appropriate compound of formula (V) to employ as a reactant to generate a given compound.

In a preferred embodiment, $R^3$ and one $R^9$ are hydrogen and the other $R^9$ and $R^5$ are methyl. In this preferred embodiment, the reactant is represented by the structure

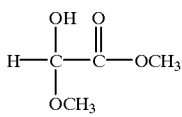

and known as glyoxylic acid methylester methylhemiacetal. It is marketed by DSM Fine Chemicals.

The process comprising reacting (A) and (B) is conducted at temperatures ranging from ambient up to the lowest decomposition temperature of any of the reactants, usually from about 60° C. to about 220° C., more often from about 120° C. to about 180° C., preferably up to about 160° C. When the reaction is conducted in the presence of organic sulfonic acid or mineral acid catalyst, the reaction is usually conducted at temperatures up to about 160° C. The process employs from about 0.6 moles of reactant (B) per mole of olefinic compound (A), up to 3 moles (B) per equivalent of (A). In one embodiment the process employs from about 0.8 moles (B) per mole of (A) to about 1.2 moles (B) per equivalent of (A), even more often from about 0.95 moles (B) per mole of (A) to about 1.05 moles (B) per equivalent of (A). In another embodiment the process employs more than 1.5 moles, preferably from about 1.6 to about 3 moles of reactant (B) per equivalent of reactant (A), more often from about 1.8 to about 2.5 moles of (B) per equivalent of (A) and preferably from about 1.9 to about 2.1 moles (B) per equivalent of (A). Removal of distillate, either from reactants or which is generated during reaction, at moderate temperatures is attainable employing reduced pressure, a solvent that aids in azeotropic distillation, or by purging with an inert gas such as $N_2$.

The progress of the reaction of (A) and (B) can be followed by observing the infra-red spectrum. The absorption for —COOH carbonyl of the products appears at about 1710 cm$^{-1}$. The total acid number as measured using essentially the procedure in ASTM D-664 (Potentiometric Method) or ASTM D-974 (Color Indicator Method) is useful together with the infrared, keeping in mind that non-acidic products (e.g., polyester products), those derived from non-acidic reactants and condensation products such as lactones will not display significant acid numbers.

These ASTM procedures appear in the Annual Book of ASTM Standards, Volume 05.01, ASTM, 1916 Race Street, Philadelphia, Pa., U.S.A.

As noted hereinabove, products obtained by the process of this invention are provided.

The following examples are intended to illustrate several intermediate compositions of this invention as well as means for preparing same. Unless indicated otherwise all parts are parts by weight, filtrations are conducted employing a diatomaceous earth filter aid, and analytical values are by analysis. The abbreviations GPC and VPO refer to gel permeation chromatography and vapor phase osmometry, respectively, both procedures being used to determine molecular weight. The abbreviation TLC-FID refers to thin layer chromatography using a flame ionization detector. TLC-FID is used to determine amounts of unreacted olefinic reactant. Saponification numbers are determined using ASTM Procedure D-94. It is to be understood that these examples are not intended to limit the scope of the invention.

EXAMPLE 1-A

A reactor is charged with 250 parts of polyisobutylene (Glissopal ES3250, BASF) having $\overline{M}_n$ about 1000 and containing about 75 mole percent terminal vinylidene groups, 60 parts glyoxylic acid, methyl ester, methyl hemiacetal (GMHA) and 1.5 part 70% aqueous methane sulfonic acid. These are heated with mixing, under $N_2$, to 120° C. and are held at temperature for a total of 6 hours, collecting 11.2 parts distillate. The temperature is increased 160° C. and held there for 6 hours, collecting 4 parts distillate, then for 7 more hours, collecting 0.7 parts distillate. The materials are mixed and heated with 50 parts water at 100° C. for 7 hours, collecting 21.2 parts distillate. The materials are stripped to 130° C. at 25 mm Hg and filtered. $\overline{M}_n$ (GPC): 98.6%=1385.

EXAMPLE 2-A

A reactor is charged with 2088 parts of polyisobutylene (Glissopal 1000) having $\overline{M}_n$ about 1000 and about 90% terminal vinylidine groups, 288 parts GMHA, 3 parts 70% aqueous methane sulfonic acid, and 0.1 parts silicone antifoam. The materials are heated with mixing under $N_2$, to 135° C. and are held at temperature for 6 hours, collecting 85 parts distillate. The materials are heated to 145° C. and filtered. The filtrate has saponification number=43.7, and contains 14.4% unreacted polyisobutylene.

EXAMPLE 3-A

A reactor is charged with 650 parts of the polyisobutylene used in Example 2-A, 78 parts GMHA, 6 parts titanium isopropoxide and 0.1 part silicone antifoam. The materials are heated, under $N_2$, to 125° C. and held at temperature for 6 hours while collecting 32 parts distillate. The materials are filtered at 125° C. The product has saponification number= 31.9, and contain 49.9% unreacted polyisobutylene.

EXAMPLE 4-A

A reactor is charged with 350 parts of polyisobutylene (Glissopal ES3252) having $\overline{M}_n$ about 2,400 and containing about 70 mole percent terminal vinylidine groups, 21 parts GMHA, 2 parts 70% aqueous methane sulfonic acid, and 0.1 part silicone antifoam. The materials are heated, under $N_2$, to 120° C. and reacted at 120° C. for 7 hours. The materials are stripped to 120° C. and 25 mm Hg and filtered. The filtrate has saponification number=17.9, and unreacted polyisobutylene about 20.3%.

EXAMPLE 5-A

A reactor is charged with 810 parts of the polyisobutylene of Example 4-A, 81 parts GMHA, 5 parts methane sulfonic acid and 0.1 part silicone antifoam. The materials are heated to 125° C., under $N_2$, and heated for 6 hours at 125° C. collecting distillate in a Dean-Stark trap. The materials are filtered at 140° C. The filtrate has saponification number= 49.3 and 7.4% unreacted polyisobutylene.

EXAMPLE 6-A

A reactor is charged with 350 parts polyisobutylene (Ultravis 10, BP Chemicals) having $\overline{M}_n$ about 1,000 and containing about 80 mole percent terminal vinylidene groups, 50.4 parts GMHA, and 4 parts 70% aqueous methane sulfonic acid. The materials are heated, under $N_2$, to 120° C. and are then reacted at 120° C. for a total of 10 hours while collecting distillate. The materials are stripped to 120° C. and 5 mm Hg and filtered. The filtrate contains 12.7% unreacted polyisobutylene and has saponification number= 44.

EXAMPLE 7-A

A reactor is charged with 5275 parts of the polyisobutylene of Example 6-A, 760 parts GMHA, 20 parts methane sulfonic acid, and 0.1 part silicone antifoam. The materials are heated, under $N_2$, to 135° C. and are held at temperature for 6 hours while collecting 210.5 parts distillate. The materials are then stripped to 135° C. at 10 mm Hg for 3 hours then filtered. The filtrate has saponification number=66.3, and 12.9% unreacted polyisobutylene.

EXAMPLE 8-A

The procedure of Example 7-A is repeated except the reaction and stripping is conducted at 140° C. The product has saponification number=91.3 and 15.4% unreacted polyisobutylene.

EXAMPLE 9-A

The procedure of Example 7-A is repeated except the reaction is conducted at 160° C. and stripping is to 145° C. at 30 mm Hg the product has saponification number=55 and contains 8.6% unreacted polyisobutylene.

EXAMPLE 10-A

A reactor is charged with 1067 parts of the polyisobutylene of Example 7-A, 154 parts GMHA, 4 parts 70% aqueous methane sulfonic acid and 0.1 part silicone antifoam. The materials are heated, under $N_2$, to 135° C. and are held at temperature for a total of 13 hours. An additional 154 parts GMHA and 2 parts methane sulfonic acid are added and the reaction is continued at 135° C. for 7 more hours collecting distillate. The materials are stripped to 135° C. at 15 mm Hg for 3 hours and filtered at 135° C. The materials have saponification number=71 and 9.8% unreacted polyisobutylene.

EXAMPLE 11-A

A reactor is charged with 350 parts of the polyisobutylene of Example 7-A, 50.4 parts GMHA, 2 parts 70% methane sulfonic acid, 8 parts water and 0.1 part silicone antifoam. The materials are heated, under $N_2$, to 135° C. and are held at temperature while collecting 20.9 parts distillate. The materials are stripped to 135° C. at 15 mm Hg for 3 hours then filtered. The filtrate has saponification number=50.5 and 7.2% unreacted polyisobutylene.

EXAMPLE 12-A

A reactor is charged with 1350 parts polyisobutylene (Glissopal 2300, BASF) having $\overline{M}_n$ about 2300 and about 90% terminal vinylidine groups, 66.1 parts GMHA and 3.5 parts 70% aqueous methane sulfonic acid. The materials heated, under $N_2$, to 135° C. and are held at temperature for 7 hours while collecting distillate. The materials are stripped to 145° C. at 25 mm Hg for 0.5 hour then filtered. The filtrate has saponification number=16.5 and 22.7% unreacted polyisobutylene.

EXAMPLE 13-A

A reactor is charged with 699 parts of the polyisobutylene of Example 12-A, 38.1 parts GMHA, 2 parts 70% aqueous methane sulfonic acid and 0.1 part silicone antifoam. The materials are heated, under $N_2$, to 135° C. and are held at temperature for a total of 9 hours while collecting distillate. The materials are filtered. The filtrate has saponification number=20 and 57% unreacted polyisobutylene.

EXAMPLE 14-A

The procedure of Example 12-A is repeated employing 1547 parts of Glissopal 2300, 126.2 parts GMHA, and 4 parts methane sulfonic acid. The product has saponification number=35 and 3.1% unreacted polyisobutylene.

EXAMPLE 15-A

A reactor is charged with 1000 parts of the polyisobutylene of Example 12-A, 54.4 parts GMHA, 4 parts titanium isopropoxide and 0.1 part silicone antifoam. The materials are heated, under $N_2$, to 125° C. and are held at temperature for 6 hours while collecting 20 parts distillate. The materials are stripped to 125° C. at 15 mm Hg for 1 hour then filtered. The filtrate has saponification number 7.3 and 78.95% unreacted polyisobutylene.

EXAMPLE 16-A

The procedure of Example 12-A is followed employing 2206 parts of the polyisobutylene of Example 12-A, 240 parts GMHA, 3 parts methane sulfonic acid and 0.1 part silicone antifoam. The materials have saponification number=42 and 1.8% unreacted polyisobutylene.

EXAMPLE 17-A

A reactor is charged with 3924 parts of the polyisobutylene of Example 12-A, 320.2 parts GMHA, 12 parts methane sulfonic acid, and 0.2 parts silicone antifoam. The materials are heated, under $N_2$, to 135° C. and are held at temperature for 6 hours while collecting distillate. The materials are stripped to 135° C. at 20 mm Hg for 1 hour, the residue is diluted with 2772 parts mineral oil diluent then filtered. The product has saponification number=19.5 and has 7.2% unreacted polyisobutylene.

EXAMPLE 18-A

A reactor is charged with 55 parts of Trilene® 67, and ethylene-propylene-ethylenenorbornene terpolymer having a viscosity average molecular weight of about 7500 and an iodine number of 19, and 165.6 parts mineral oil. The materials are heated to 110° C. under $N_2$ followed by addition of 3.3 parts GMHA and 0.21 parts 70% aqueous methane sulfonic acid. The materials are heated to 145° C. and held at temperature for 6 hours followed by stripping at 145° C. and 12 mm Hg for 1 hour.

EXAMPLE 19-A

A reactor is charged with 350 parts of a polyisobutene having $\overline{M}_n$=940 (VPO) and bromine number=17, 42 parts GMHA and 0.5 parts 70% aqueous methane sulfonic acid. The materials are heated, under N2, to 135° C. and maintained at temperature for 6 hours while collecting 12.1 parts distillate. The materials are filtered at 135° C. The product has saponification number=50 and has 29.3% unreacted polyisobutene.

EXAMPLE 20-A

The procedure of Example 19-A is repeated employing 525 parts of a polyisobutene having $\overline{M}_n$=1700 (VPO) and bromine number=6, 63 parts GMHA and 1.0 part methane sulfonic acid. The product has saponification number=44 and contains 19.4% unreacted polyisobutene.

Also contemplated herein is a process which further comprises reacting the product of the reaction of reactants (A) and (B) with (C) ammonia, hydrazine or an amine having at lest one condensable N—H group and/or (D) a reactive metal or a reactive metal compound. Products obtained thereby are useful as performance improving additives for lubricating oil compositions and for normally liquid fuels.

Suitable reactants (C) and (D) are described hereinbelow.

(C) Ammonia, Hydrazine and Amine Reactants

Suitable (C) reactants, as defined herein, include ammonia, hydrazines, monoamines or polyamines. The (C) reactants must contain at least one condensable N—H group. The monoamines generally contain from 1 to about 24 carbon atoms, preferably 1 to about 12, and more preferably 1 to about 6. Examples of monoamines useful in the present invention include primary amines, for example methylamine, ethylamine, propylamine, butylamine, octylamine, and dodecylamine. Examples of secondary amines include dimethylamine, diethylamine, dipropylamine, dibutylamine, methylbutylamine, ethylhexylamine, etc. Tertiary monoamines will not result in formation of an amide, but can form salts with carboxylic acids.

In another embodiment, the monoamine may be a hydroxyamine. Typically, the hydroxyamines are primary or secondary alkanolamines or mixtures thereof. As stated above, tertiary monoamines will not react to form amides; however tertiary alkanol monoamines sometimes can react to form a tertiary amino group containing ester. Alkanol amines that can react to form amide can be represented, for example, by the formulae:

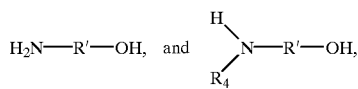

wherein each $R_4$ is independently a hydrocarbyl group of one to about 22 carbon atoms or hydroxyhydrocarbyl group of two to about 22 carbon atoms, preferably one to about four, and R' is a divalent hydrocarbyl group of about two to about 18 carbon atoms, preferably two to about four. The group —R'—OH in such formulae represents the hydroxyhydrocarbyl group. R' can be an acyclic, alicyclic or aromatic group. Typically, R' is an acyclic straight or branched alkylene group such as an ethylene, 1,2-propylene, 1,2-butylene, 1,2-octadecylene, etc. group. When two $R^4$ groups are present in the same molecule they can be joined by a direct carbon-to-carbon bond or through a heteroatom (e.g., oxygen, nitrogen or sulfur) to form a 5-, 6-, 7- or 8-membered ring structure. Examples of such heterocyclic amines include N-(hydroxyl lower alkyl)-morpholines, -thiomorpholines, -piperidines, -oxazolidines, -thiazolidines and the like. Typically, however, each $R^4$ is independently a methyl, ethyl, propyl, butyl, pentyl or hexyl group.

Examples of these alkanolamines include mono-, di-, and triethanolamine, diethylethanolamine, ethylethanolamine, butyldiethanolamine, etc.

The hydroxyamines can also be ether N-(hydroxyhydrocarbyl)amines. These are hydroxy poly (hydrocarbyloxy) analogs of the above-described hydroxy amines (these analogs also include hydroxyl-substituted oxyalkylene analogs). Such N-(hydroxyhydrocarbyl)amines can be conveniently prepared, for example, by reaction of epoxides with aforedescribed amines and can be represented by the formulae:

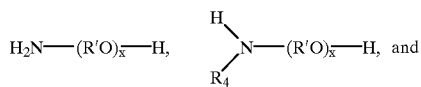

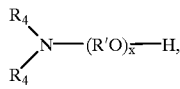

wherein x is a number from about 2 to about 15 and $R_4$ and R' are as described above. $R_4$ may also be a hydroxypoly (hydrocarbyloxy) group.

Other useful amines include ether amines of the general formula $$R_6OR_1NHR_7$$

wherein $R^6$ is a hydrocarbyl group, preferably an aliphatic group, more preferably an alkyl group, containing from 1 to about 24 carbon atoms, $R_1$ is a divalent hydrocarbyl group, preferably an alkylene group, containing from two to about 18 carbon atoms, more preferably two to about 4 carbon atoms and $R_7$ is H or hydrocarbyl, preferably H or aliphatic, more preferably H or alkyl, more preferably H. When $R_7$ is not H, then it preferably is alkyl containing from one to about 24 carbon atoms. Especially preferred ether amines are those available under the name SURFAM produced and marketed by Sea Land Chemical Co., Westlake, Ohio.

The amine may also be a polyamine. The polyamine may be aliphatic, cycloaliphatic, heterocyclic or aromatic. Examples of the polyamines include alkylene polyamines, hydroxy containing polyamines, arylpolyamines, and heterocyclic polyamines.

Alkylene polyarnines are represented by the formula

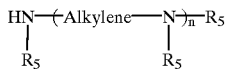

wherein n has an average value between about 1 and about 10, preferably about 2 to about 7, more preferably about 2 to about 5, and the "Alkylene" group has from 1 to about 10 carbon atoms, preferably about 2 to about 6, more preferably about 2 to about 4. $R_5$ is independently hydrogen or an aliphatic or hydroxy-substituted aliphatic group of up to about 30 carbon atoms. Preferably $R_5$ is H or lower alkyl, most preferably, H.

Alkylene polyamines include methylene polyamines, ethylene polyamines, butylene polyamines, propylene polyamines, pentylene polyamines, etc. Higher homologs and related heterocyclic amines such as piperazines and N-amino alkyl-substituted piperazines are also included. Specific examples of such polyamines are ethylene diamine, diethylene triamine, triethylene tetramine, tris-(2-aminoethyl)amine, propylene diamine, trimethylene diamine, tripropylene tetramine, tetraethylene pentamine, hexaethylene heptamine, pentaethylenehexamine, aminoethyl piperazine, dimethyl aminopropylamine, etc.

Higher homologs obtained by condensing two or more of the above-noted alkylene amines are similarly useful as are mixtures of two or more of the aforedescribed polyamines.

Ethylene polyamines, such as some of those mentioned above, are preferred. They are described in detail under the heading Ethylene Amines in Kirk Othmer's "Encyclopedia of Chemical Technology", 2d Edition, Vol. 7, pages 22–37, Interscience Publishers, New York (1965). Such polyamines are most conveniently prepared by the reaction of ethylene dichloride with ammonia or by reaction of an ethylene imine with a ring opening reagent such as water, ammonia, etc. These reactions result in the production of a complex mixture of polyalkylene polyamines including cyclic condensation products such as the aforedescribed piperazines. Ethylene polyamine mixtures are useful.

Other useful types of polyamine mixtures are those resulting from stripping of the above-described polyamine mixtures to leave as residue what is often termed "polyamine bottoms". In general, alkylene polyamine bottoms can be characterized as having less than two, usually less than 1% (by weight) material boiling below about 200° C. A typical sample of such ethylene polyamine bottoms obtained from the Dow Chemical Company of Freeport, Tex., designated "E-100" has a specific gravity at 15.6° C. of 1.0168, a percent nitrogen by weight of 33.15 and a viscosity at 40° C. of 121 centistokes. Gas chromatography analysis of such a sample contains about 0.93% "Light Ends" (most probably diethylenetriamine), 0.72% triethylenetetramine, 21.74% tetraethylene pentaamine and 76.61% pentaethylene hexamine and higher (by weight). These alkylene polyamine bottoms include cyclic condensation products such as piperazine and higher analogs of diethylenetriamine, triethylenetetramine and the like.

Another useful polyamine is a condensation product obtained by reaction of at least one hydroxy compound with at least one polyamine reactant containing at least one primary or secondary amino group. The hydroxy compounds are preferably polyhydric alcohols and amines. Preferably the hydroxy compounds are polyhydric amines. Polyhydric amines include any of the above-described monoamines reacted with an alkylene oxide (e.g., ethylene oxide, propylene oxide, butylene oxide, etc.) having two to about 20 carbon atoms, preferably two to about four. Examples of polyhydric amines include tri-(hydroxypropyl) amine, tris-(hydroxymethyl)amino methane, 2-amino-2-methyl-1,3-propanediol, N,N,N',N'-tetrakis(2-hydroxypropyl)ethylenediamine, and N,N,N',N'-tetrakis(2-hydroxyethyl) ethylenediamine.

Polyamine reactants, which react with the polyhydric alcohol or amine to form the condensation products or condensed amines, are described above. Preferred polyamine reactants include triethylenetetramine (TETA), tetraethylenepentamine (TEPA), pentaethylenehexamine (PEHA), and mixtures of polyamines such as the above-described "amine bottoms".

The condensation reaction of the polyamine reactant with the hydroxy compound is conducted at an elevated temperature, usually about 60° C. to about 265° C. in the presence of an acid catalyst.

The amine condensates and methods of making the same are described in Steckel (U.S. Pat. No. 5,053,152) which is incorporated by reference for its disclosure to the condensates and methods of making.

In another embodiment, the polyamines are hydroxy-containing polyamines. Hydroxy-containing polyamine analogs of hydroxy monoamines, particularly alkoxylated alkylenepolyamines can also be used. Such polyamines can be made by reacting the above-described alkylene amines with one or more of the above-described alkylene oxides. Similar alkylene oxide-alkanolamine reaction products can also be used such as the products made by reacting the aforedescribed primary, secondary or tertiary alkanolamines with ethylene, propylene or higher epoxides in a 1.1 to 1.2 molar ratio. Reactant ratios and temperatures for carrying out such reactions are known to those skilled in the art.

Specific examples of alkoxylated alkylenepolyamines include N-(2-hydroxyethyl)ethylenediamine, N,N-di-(2-hydroxyethyl)-ethylenediamine, 1-(2-hydroxyethyl) piperazine, mono-(hydroxypropyl)-substituted tetraethylenepentamine, N-(3-hydroxybutyl)-tetramethylene diamine, etc. Higher homologs obtained by condensation of the above illustrated hydroxy-containing polyamines through amino groups or through hydroxy groups are likewise useful. Condensation through amino groups results in a higher amine accompanied by removal of ammonia while condensation through the hydroxy groups results in products containing ether linkages accompanied by removal of water. Mixtures of two or more of any of the aforesaid polyamines are also useful.

In another embodiment, the polyamine may be a heterocyclic polyamine. The heterocyclic polyamines include aziridines, azetidines, azolidines, tetra- and dihydropyridines, pyrroles, indoles, piperidines, imidazoles, di- and tetrahydroimidazoles, piperazines, isoindoles, purines, N-aminoalkylmorpholines, N-aminoalkylthiomorpholines, N-aminoalkylpiperazines, N,N'-bisaminoalkyl piperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, or nitrogen with oxygen and/or sulfur in the hetero ring, especially the piperidines, piperazines, thiomorpholines, morpholines, pyrrolidines, and the like. Piperidine, aminoalkylsubstituted piperidines, piperazine, aminoalkylsubstituted piperazines, morpholine, aminoalkyl-substituted morpholines, pyrrolidine, and aminoalkyl-substituted pyrrolidines, are especially preferred. Usually the aminoalkyl substituents are substituted on a nitrogen atom forming part of the hetero ring. Specific examples of such heterocyclic amines include N-aminopropylmorpholine, N-amino-ethylpiperazine, and N,N'-diaminoethyl-piperazine. Hydroxy alkyl substituted heterocyclic polyamines are also useful. Examples include N-hydroxyethylpiperazine and the like.

In another embodiment, the amine is a polyalkene-substituted amine. These polyalkene-substituted amines are well known to those skilled in the art. They are disclosed in U.S. Pat. Nos. 3,275,554; 3,438,757; 3,454,555; 3,565,804; 3,755,433; and 3,822,289. These patents are hereby incorporated by reference for their disclosure of polyalkene-substituted amines and methods of making the same.

Typically, polyalkene-substituted amines are prepared by reacting halogenated-, preferably chlorinated-, olefins and olefin polymers (polyalkenes) with amines (mono- or polyamines). The amines may be any of the amines described above. Examples of these compounds include poly(propylene)amine; N,N-dimethyl-N-poly(ethylene/propylene)amine, (50:50 mole ratio of monomers); polybutene amine; N,N-di(hydroxyethyl)-N-polybutene amine; N-(2-hydroxypropyl)-N-polybutene amine; N-polybutene-aniline; N-polybutene-morpholine; N-poly(butene) ethylenediamine; N-poly(propylene)trimethylenediamine; N-poly(butene)diethylene-triamine; N',N'-poly(butene) tetraethylenepentamine; N,N-dimethyl-N'-poly-(propylene)-1,3-propylenediamine and the like.

The polyalkene substituted amine is characterized as containing from at least about 8 carbon atoms, preferably at least about 30, more preferably at least about 35 up to about 300 carbon atoms, preferably 200, more preferably 100. In one embodiment, the polyalkene substituted amine is characterized by an n (number average molecular weight) value of at least about 500. Generally, the polyalkene substituted amine is characterized by an n value of about 500 to about 5000, preferably about 800 to about 2500. In another embodiment n varies between about 500 to about 1200 or 1300.

The polyalkenes from which the polyalkene substituted amines are derived include homopolymers and interpolymers of polymerizable olefin monomers of 2 to about 16 carbon atoms; usually 2 to about 6, preferably 2 to about 4, more preferably 4. The olefins may be monoolefins such as ethylene, propylene, 1-butene, isobutene, and 1-octene; or a polyolefinic monomer, preferably diolefinic monomer, such 1,3-butadiene and isoprene. Preferably, the polymer is a homopolymer. An example of a preferred homopolymer is a polybutene, preferably a polybutene in which about 50% of the polymer is derived from isobutylene. The polyalkenes are prepared by conventional procedures.

Another useful reactant (C) is an acylated polyamine. These include reaction products of carboxylic acids with an excess of polyamine to form an acylated nitrogen compound such as an amide or imide that has at least one condensable N—H group available for reaction with the product obtained from the reaction of (A) and (B).

To form this reactant, virtually any acylating agent may be used such as fatty acids, polyolefin substituted succinic acids and anhydrides, and the like. Preferred are polyisobutylene succinic acids and anhydrides wherein the polyisobutylene substituent is derived from polyisobutylene having $\overline{M}_n$ ranging from about 500 to about 2500.

It is generally preferred to utilize sufficient amine reactant (C) to convert substantially all of the intermediate arising from reaction of (A) with (B) to product; however, conversion of at least 50%, more preferably 75% is often acceptable. Preferably, at least 90%, more preferably 99–100% conversion is effected.

The reaction with the (C) reactant to prepare the products of this invention is conducted at temperatures ranging from about 25° C. to about 230° C. When the amine is an alkanolamine, an alkylene polyamine or a thioalkanol amine, N-containing heterocyclic group containing products such as imidazoline, oxazoline, or thiazoline formation may form. These are frequently obtained by first preparing an amide then continuing the reaction at elevated temperature to generate imidazoline, thiazoline or oxazoline by removal of water.

Imidazoline formation will not occur with every amine; the amine must have the structural element:

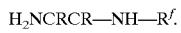

H$_2$NCRCR—NH—R$^f$.

Similarly, oxazoline formation can take place when the amine is a β-hydroxyethyl amine, e.g.,

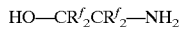

HO—CR$^f_2$CR$^f_2$—NH$_2$

β-thiolamines can react to form thiazolines.

In the above formulae, each R$^f$ is independently H, alkoxyalkyl, hydroxyalkyl, hydrocarbyl, aminohydrocarbyl or N-alkoxyalkyl- or hydroxyalkyl-substituted amino hydrocarbyl.

Thus, if imidazoline, thiazoline or oxazoline formation is not desired, they may be avoided by employing amine reactants that do not provide the opportunity for imidazoline, thiazoline or oxazoline formation, or, if the amine employed can lead to oxazoline, thiazoline or imidazoline, to minimize formation thereof by conducting the reaction at the lowest temperature to prepare amide at an acceptable rate and in acceptable amounts, or to avoid prolonged heating of the amide-containing product, once it has formed. Infrared analysis during the reaction is a convenient means for determining the nature and extent of the reaction.

The product formed from the reaction of (A) and (B) is then reacted, at temperatures ranging from about 25° C. to about 230° C., preferably from about 60° C. to about 150° C., more often from about 100° C. to about 110° C. with (C) ammonia, a hydrazine or an amine characterized by the presence within its structure of at least one N—H group. Reactant (C) is used in amounts ranging from about 0.5 equivalents up to about 2 moles, per mole of (B).

Products obtained by post-treating the acylated nitrogen compounds of this invention are also useful. Reagents such as urea, thiourea, carbon disulfide, aldehydes, ketones, carboxylic acids, hydrocarbon substituted succinic anhydrides, nitrites, epoxides, boron compounds, phosphorus compounds and the like are useful post-treating agents.

The Reactive Metals and Metal Compounds

The reactive metals include but are not limited to alkali metals, alkaline earth metals, zinc, cadmium, lead, cobalt, nickel iron, manganese and copper. Preferred are the alkali and alkaline earth metals. Especially preferred are sodium, potassium, calcium and lithium.

Examples of reactive metal compounds are sodium oxide, sodium hydroxide, sodium carbonate, sodium methylate, sodium phenoxide, corresponding potassium and lithium compounds, calcium oxide, calcium hydroxide, calcium carbonate, calcium methylate, calcium chloride, calcium phenoxide, and corresponding barium and magnesium compounds, zinc oxide, zinc hydroxide, zinc carbonate, cadmium chloride, lead oxide, lead hydroxide, lead carbonate, nickel oxide, nickel hydroxide, nickel nitrate, cobalt oxide, ferrous carbonate, ferrous oxide, cupric acetate, cupric nitrate, etc.

The above metal compounds are merely illustrate of those useful in this invention; however, the invention is not considered as limited to such. Suitable metals and metal containing reactants are disclosed in many U.S. patents including U.S. Pat. Nos. 3,306,908; 3,271,310; and U.S. Pat. No. Re. 26,433.

The reaction product resulting from the reaction of the condensation product and the reactive metal or metal compound will preferably comprise a substantially neutral metal salt, which metal salt is a carboxylate and/or phenate. However, the salts may contain up to about 50% unreacted lactone, carboxylic acid, or ester group of mixtures thereof.

It is also to be understood that the salts of Formula (I) may also be slightly basic, that is they may contain a small excess (up to about 10–15% excess) of metal beyond that which is normally expected based on the stoichiometry of the components. The excess metal is not used for the purpose of preparing overbased metals but for insuring that the reaction leading to salt formation reaction is driven to completion.

The following examples are intended to illustrate several derivatives of this invention as well as means for preparing same. Unless indicated otherwise all parts are parts by weight, filtrations are conducted employing a diatomaceous earth filter aid, and analytical values are by actual analysis. The abbreviations GPC and VPO refer to gel permeation chromatography and vapor phase osmometry, respectively, both procedures being used to determine molecular weight. Aromatic hydrocarbons are commercial aromatic hydrocarbon solvents having a flash point of about 43° C. It is to be understood that these examples are intended to illustrate several compositions and procedures of the invention and are not intended to limit the scope of the invention.

EXAMPLE 1-B

A reactor is charged 225 parts of the product of Example 4-A, 4.6 parts of an ethylene polyamine mixture having an average compositions corresponding to tetraethylenepentamine, and 153.1 parts mineral oil diluent.

The materials are heated, under nitrogen, for 6 hours at 160° C. while collecting distillate in a Dean-Stark trap. The materials are filtered at 140° C. The product has percent nitrogen=0.33.

EXAMPLE 2-B

The process of Example 1-B is repeated employing 500 parts of the product of Example 5-A, 28.2 parts of the polyamine and 352.1 parts mineral oil diluent. The product contains 1.03% nitrogen.

EXAMPLE 3-B

The process of Example 1-B is repeated employing 350 parts of the product of Example 7-A, 19.9 parts of the polyamine and 246.6 parts mineral oil diluent. The product contains 1.0% nitrogen.

EXAMPLE 4-B

The process of Example 1-B is repeated employing 350 parts of the product of Example 7-A, 27.4 parts of the polyamine and 251.6 parts mineral oil diluent. The product contains 1.3% nitrogen.

EXAMPLE 5-B

The process of Example 1-B is repeated employing 350 parts of the product of Example 7-A, 29.9 parts of the polyamine and 253.3 parts mineral oil diluent. The product contains 1.42% nitrogen.

EXAMPLE 6-B

The process of Example 1-B is repeated employing 230 parts of the product of Example 8-A, 24.7 parts of the polyamine and 169.8 parts mineral oil diluent. The product contains 2.01% nitrogen.

EXAMPLE 7-B

A reactor is charged with 600 parts of the products of Example 12-A, 14.6 parts of a polyamine bottoms containing about 31.5% nitrogen (HPA-X, Union Carbide) and 410 parts mineral oil diluent. The materials are heated for 6 hours, under $N_2$, at 160° C. and filtered. The filtrate contains 0.45% nitrogen.

EXAMPLE 8-B

The process of Example 7-B is repeated employing 300 parts of the product of Example 13-A, 12.3 parts of the polyamine bottoms and 208 parts of mineral oil diluent. The product contains 0.72% nitrogen.

EXAMPLE 9-B

The process of Example 7-B is repeated employing 5100 parts of the product of Example 17-A, 132.6 parts of the polyamine bottoms and 88.4 parts of mineral oil diluent. The reaction is conducted at 170° C. for 7 hours and the filtration is done at 145° C. The product contains 0.81% nitrogen.

EXAMPLE 10-B

A reactor is charged with 300 parts of the product of Example 13-A, 10.8 parts of the polyamine bottoms of Example 7-B, 8.9 parts of N-tallow propanediamine (Duomeen T, Akzo) and 213 parts mineral oil diluent. The materials are heated to 180° C. and maintained at temperature for 6 hours while collecting distillate. The materials are filtered at 150° C. The product contains 0.78% nitrogen.

EXAMPLE 11-B

A reactor is charged with 224 parts of the product of Example 18-A, 85 parts of a 60% by weight in oil solution of the reaction product of a polyisobutene ($\overline{M}_n$ 1000) substituted succinic anhydride with the condensation product of an ethylene polyamine bottoms with tris-hydroxymethylaminomethane. The materials are reacted, under $N_2$, at 165° C. for 5 hours, followed by dilution in 165.6 parts mineral oil. The solution is filtered through cloth. The filtrate contains 0.377% nitrogen.

EXAMPLE 12-B

A reactor is charged with 500 parts of polyisobutylene (Ultravis 10), 72 parts GMHA and 2 parts 70% aqueous methane sulfonic acid. The materials are heated under $N_2$ to 160° C. and maintained at temperature for 6 hours while collecting distillate in a Dean-Stark trap. To this material are added 41.9 parts N-aminoethylpiperazine over 0.1 hour followed by reaction at 160° C. for 5 hours while collecting distillate. The materials are diluted with 248.1 parts aromatic diluent and filtered. The filtrate contains 1.54% nitrogen.

EXAMPLE 13-B

A reactor is charged with 600 parts of the product of Example 2-A and 8 parts $Ca(OH)_2$ followed by heating at 150° C. for 4 hours, dilution with 200 part mineral oil and filtration The Lubricating Oil Compositions The Oil of Lubricating Viscosity In one embodiment of this invention, the compositions are used as additives in lubricating oil compositions. The lubricating compositions employ an oil of lubricating viscosity, including natural or synthetic lubricating oils and mixtures thereof. Mixtures of mineral oil and synthetic oils, particularly polyalphaolefin oils and polyester oils, are often used. The lubricating composition of this invention comprise a major amount of an oil of lubricating viscosity and a minor amount of the composition of this invention.

By major amount is meant greater than 50% by weight, while minor amount means less than 50% by weight, based on the total weight of the composition.

Natural oils include animal oils and vegetable oils (e.g. castor oil, lard oil and other vegetable acid esters) as well as mineral lubricating oils such as liquid petroleum oils and solvent-treated or acid treated mineral lubricating oils of the paraffinic, naphthenic or mixed paraffinic-naphthenic types. Hydrotreated or hydrocracked oils are included within the scope of useful oils of lubricating viscosity.

Oils of lubricating viscosity derived from coal or shale are also useful. Synthetic lubricating oils include hydrocarbon oils and halosubstituted hydrocarbon oils such as polymerized and interpolymerized olefins, etc. and mixtures thereof, alkylbenzenes, polyphenyl, (e.g., biphenyls, terphenyls, alkylated polyphenyls, etc.), alkylated diphenyl ethers and alkylated diphenyl sulfides and their derivatives, analogs and homologues thereof and the like.

Alkylene oxide polymers and interpolymers and derivatives thereof, and those where terminal hydroxyl groups have been modified by esterification, etherification, etc., constitute other classes of known synthetic lubricating oils that can be used.

Another suitable class of synthetic lubricating oils that can be used comprises the esters of dicarboxylic acids and those made from $C_5$ to $C_{12}$ monocarboxylic acids and polyols or polyol ethers.

Other synthetic lubricating oils include liquid esters of phosphorus-containing acids, polymeric tetrahydrofurans and the like, silicon-based oils such as the polyalkyl-, polyaryl-, polyalkoxy-, or polyaryloxy-siloxane oils and silicate oils.

Hydrotreated naphthenic oils are well known.

Unrefined, refined and rerefined oils, either natural or synthetic (as well as mixtures of two or more of any of these) of the type disclosed hereinabove can used in the compositions of the present invention. Unrefined oils are those obtained directly from a natural or synthetic source without further purification treatment. Refined oils are similar to the unrefined oils except they have been further treated in one or more purification steps to improve one or more properties. Rerefined oils are obtained by processes similar to those used to obtain refined oils applied to refined oils which have been already used in service. Such rerefined oils often are additionally processed by techniques directed to removal of spent additives and oil breakdown products.

Specific examples of the above-described oils of lubricating viscosity are given in Chamberlin III, U.S. Pat. No. 4,326,972 and European Patent Publication 107,282, both of which are hereby incorporated by reference for relevant disclosures contained therein.

A basic, brief description of lubricant base oils appears in an article by D. V. Brock, "Lubrication Engineering", Volume 43, pages 184–5, March, 1987, which article is expressly incorporated by reference for relevant disclosures contained therein.

Other Additives

The lubricating oil compositions of this invention may contain minor amounts of other components. The use of such components is optional and the presence thereof in the compositions of this invention will depend on the particular use and level of performance required. Thus these components may be included or excluded.

The compositions may comprise a zinc salt of a dithiophosphoric acid. Zinc salts of dithiophosphoric acids are often referred to as zinc dithiophosphates, zinc O,O-dihydrocarbyl dithiophosphates, and other commonly used names. They are sometimes referred to by the abbreviation ZDP. One or more zinc salts of dithiophosphoric acids may be present in a minor amount to provide additional extreme pressure, anti-wear and anti-oxidancy performance.

In addition to zinc salts of dithiophosphoric acids discussed hereinabove, other additives that may optionally be used in the lubricating oils of this invention include, for example, detergents, dispersants, viscosity improvers, oxidation inhibiting agents, metal passivating agents, pour point depressing agents, extreme pressure agents, anti-wear agents, color stabilizers and anti-foam agents. The above-mentioned dispersants and viscosity improvers are used in addition to the additives of this invention.

Auxiliary extreme pressure agents and corrosion and oxidation inhibiting agents which may be included in the compositions of the invention are exemplified by chlorinated aliphatic hydrocarbons, organic sulfides and polysulfides, phosphorus esters including dihydrocarbon and trihydrocarbon phosphites, molybdenum compounds, and the like.

Viscosity improvers (also sometimes referred to as viscosity index improvers) may be included in the compositions of this invention. Viscosity improvers are usually polymers, including polyisobutenes, polymethacrylic acid esters, diene polymers, polyalkyl styrenes, alkenylarene-conjugated diene copolymers and polyolefins. Multifunctional viscosity improvers, other than those of the present invention, which also have dispersant and/or antioxidancy properties are known and may optionally be used in addition to the products of this invention. Such products are described in numerous publications including those mentioned in the Background of the Invention. Each of these publications is hereby expressly incorporated by reference.

Pour point depressants are a particularly useful type of additive often included in the lubricating oils described herein. See for example, page 8 of 'Lubricant Additives" by C. V. Smalheer and R. Kennedy Smith (Lezius-Hiles Company Publisher, Cleveland, Ohio, 1967). Pour point depressants useful for the purpose of this invention, techniques for their preparation and their use are described in U.S. Pat. Nos. 2,387,501; 2,015,748; 2,655,479; 1,815,022; 2,191,498; 2,666,748; 2,721,877; 2,721,878; and 3,250,715 which are expressly incorporated by reference for their relevant disclosures.

Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125–162.

Detergents and dispersants may be of the ash-producing or ashless type. The ash-producing detergents are exemplified by oil soluble neutral and basic salts of alkali or alkaline earth metals with sulfonic acids, carboxylic acids, phenols or organic phosphorus acids characterized by at least one direct carbon-to-phosphorus linkage.

The term "basic salt" is used to designate metal salts wherein the metal is present in stoichiometrically larger amounts than the organic acid radical. The amount of excess metal present is denoted by the metal ratio (MR) which is defined as the percentage of metal relative to the stoichiometric amount divided by 100. A neutral salt has MR=1. One with three times the stoichiometric amount has MR=3, etc. Basic salts and techniques for preparing and using them are well known to those skilled in the art and need not be discussed in detail here.

Ashless detergents and dispersants are so-called despite the fact that, depending on its constitution, the detergent or dispersant may upon combustion yield a nonvolatile residue such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Patent number 1,306,529 and in many U.S. patents including the following:

| | | |
|---|---|---|
| 3,163,603 | 3,381,022 | 3,542,680 |
| 3,184,474 | 3,399,141 | 3,567,637 |
| 3,215,707 | 3,415,750 | 3,574,101 |
| 3,219,666 | 3,433,744 | 3,576,743 |
| 3,271,310 | 3,444,170 | 3,630,904 |
| 3,272,746 | 3,448,048 | 3,632,510 |
| 3,281,357 | 3,448,049 | 3,632,511 |
| 3,306,908 | 3,451,933 | 3,697,428 |
| 3,311,558 | 3,454,607 | 3,725,441 |
| 3,316,177 | 3,467,668 | 4,194,886 |
| 3,340,281 | 3,501,405 | 4,234,435 |
| 3,341,542 | 3,522,179 | 4,491,527 |
| 3,346,493 | 3,541,012 | RE 26,433 |
| 3,351,552 | 3,541,678 | |

(2) Reaction products of relatively high molecular weight aliphatic or alicyclic halides with amines, preferably polyalkylene polyamines. These may be characterized as "amine dispersants" and examples thereof are described for example, in the following U.S. patents:

|           |           |
|-----------|-----------|
| 3,275,554 | 3,454,555 |
| 3,438,757 | 3,565,804 |

(3) Reaction products of alkyl phenols in which the alkyl groups contains at least about 30 carbon atoms with aldehydes (especially formaldehyde) and amines (especially polyalkylene polyamines), which may be characterized as "Mannich dispersants". The materials described in the following U.S. patents are illustrative:

|           |           |
|-----------|-----------|
| 3,413,347 | 3,725,480 |
| 3,697,574 | 3,726,882 |
| 3,725,277 |           |

(4) Products obtained by post-treating the carboxylic amine or Mannich dispersants with such reagents are urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:

|           |           |           |           |
|-----------|-----------|-----------|-----------|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |
|           |           |           | 4,234,435 |

(5) Interpolymers of oil-solubilizing monomers such as decyl methacrylate, vinyl decyl ether and high molecular weight olefins with monomers containing polar substituents, e.g., aminoalkyl acrylates or methacrylates, acrylamides and poly-(oxyethylene)-substituted acrylates. These may be characterized as "polymeric dispersants" and examples thereof are disclosed in the following U.S. patents:

|           |           |
|-----------|-----------|
| 3,329,658 | 3,666,730 |
| 3,449,250 | 3,687,849 |
| 3,519,565 | 3,702,300 |

The above-noted patents are incorporated by reference herein for their disclosures of ashless dispersants.

The above-illustrated additives may each be present in lubricating compositions at a concentration of as little as 0.001% by weight usually ranging from about 0.01% to about 20% by weight, more often from about 1% to about 12% by weight.

The compositions of the present invention are present in a minor amounts, often amounts ranging from about 1% to about 20% by weight, more often from about 3% to about 10% by weight, even more often from about 5% to about 8% by weight.

Additive Concentrates

The various additives described herein can be added directly to the lubricating oil or fuel. Preferably, however, they are diluted with a substantially inert, normally liquid organic diluent such as mineral oil, naphtha, benzene, toluene or xylene, to form an additive concentrate. These concentrates usually comprise about 0.1 to about 80% by weight, frequently from about 1% to about 80% by weight, more often from about 10% to about 80% by weight, of the compositions of this invention and may contain, in addition, one or more other additives known in the art or described hereinabove. The balance comprises the normally liquid organic diluent. Concentrations such as 15%, 20%, 30% or 50% or higher may be employed.

Additive concentrates are prepared by mixing together, often at elevated temperature, the desired components.

Additive concentrates used for preparing lubricating oil compositions are illustrated by the following examples. The amounts shown are indicated as parts by weight or parts by volume. Unless indicated otherwise, components are indicated as parts or percentages by weight of chemical present on an oil or diluent free basis. When products of Examples set forth hereinabove are used, the amounts listed are as prepared, including diluent, if any. The abbreviation MR refers to metal ratio, the relative amount of metal in an overbased salt compared to the amount expected based on stoichiometry. For example, MR=2 means the overbased material contains twice the amount of metal compared to the "normal" stoichiometric amount.

Additive concentrates are prepared by blending the components listed in the following Tables. Mineral oil is used to bring the total to 100 parts.

TABLE 1

ADDITIVE CONCENTRATES

| Component | Example (Parts by Weight) | | | | | |
|---|---|---|---|---|---|---|
|  | A | B | C | D | E | F |
| Ca overbased (MR ~ 1.1) S-coupled alkyl phenate | 4.2 | 4.2 | 4.69 | 4.69 | 4.69 | 4.69 |
| Di-(nonylphenol) amine | 1.89 | 1.89 | 2.12 | 2.12 | 2.12 | 2.12 |

TABLE 1-continued

ADDITIVE CONCENTRATES

| Component | Example (Parts by Weight) | | | | | |
|---|---|---|---|---|---|---|
| | A | B | C | D | E | F |
| Ca overbased (MR ~ 2.8) alkyl benzene sulfonate | 9.95 | 9.95 | 11.17 | 11.17 | 11.17 | 11.17 |
| Mg overbased (MR ~ 14.7) alkyl benzene sulfonate | 2.18 | 2.18 | 2.44 | 2.44 | 2.44 | 2.44 |
| Silicone antifoam | 0.01 | 0.01 | 0.01 | 0.01 | 0.01 | 0.01 |
| Zinc salt of mixed isopropyl-2-ethylhexyl dithiophosphate | 8.79 | 8.79 | 9.87 | 9.87 | 9.87 | 9.87 |
| Product of Example 1-B | 54.47 | | | | | |
| Product of Example 2-B | | 54.47 | | | | |
| Product of Example 3-B | | | 48.90 | | | |
| Product of Example 4-B | | | | 48.90 | | |
| Product of Example 5-B | | | | | 48.90 | |
| Product of Example 6-B | | | | | | 48.90 |

The lubricating compositions of this invention are illustrated in the following Examples. The lubricating compositions are prepared by combining the specified ingredients, individually or from concentrates, in the indicated amounts and oil of lubricating viscosity to make the total 100 parts by weight. The amounts shown are indicated as parts by weight. Unless indicated otherwise, where components are indicated as parts by weight, they are amounts of chemical present on an oil or diluent free basis. Thus, for example, an additive comprising 50% oil used at 10% by weight in a blend, provides 5% by weight of chemical. Totals are 100% by weight or 100 parts by weight. However, when referring to incorporation of products of Examples set forth herein, amounts are as prepared, including any diluent.

EXAMPLES I–VI

Lubricating oil compositions are prepared by mixing together in a mineral oil of lubricating viscosity (Exxon 15W-40), 7.5 parts of a 91% oil solution of an ethylene-propylene-diene copolymer, 0.08% of a styrene-maleate copolymer neutralized with aminopropyl morpholine, and the indicated amount of the additive concentrates set forth in the following table:

| Additive Concentrate/Parts by Weight | |
|---|---|
| Example | |
| I | Example A/13.31 |
| II | Example B/13.31 |
| III | Example C/11.86 |
| IV | Example D/11.86 |
| V | Example E/11.86 |
| VI | Example F/11.86 |

The Fuel Compositions

The Normally Liquid Fuels

As indicated hereinabove, the products of this invention may also be used as additives for normally liquid fuels.

Fuel compositions of this invention comprise a major amount of a normally liquid fuel, i.e., one which is liquid under normal conditions of use, typically, at ambient temperature, and minor amounts of the compositions of this invention, where major amount and minor amount are as defined hereinabove.

The fuels used in the fuel compositions of this invention are well known to those skilled in the art and usually contain a major portion of a normally liquid fuel such as hydrocarbonaceous petroleum distillate fuel (e.g., motor gasoline as defined by ASTM Specifications D-439-89 and D-4814-91 and diesel fuel or fuel oil as defined in ASTM Specifications D-396-90 and D-975-91). Fuels containing non-hydrocarbonaceous materials such a alcohols, ether, organonitro compounds and the like (e.g., methanol, ethanol, diethyl ether, methyl ethyl ether, nitromethane) are also within the scope of this invention as are liquid fuels derived from vegetable or mineral sources. Vegetable or mineral sources include, for example, crude petroleum oil, coal, corn, shale, oilseeds and other sources.

Oxygenates are compounds covering a range of alcohol and ether type base fuel. They have also been used as the sole fuel component, but more often as a supplemental fuel used together with, for example, gasoline to form the well-known "gasohol" blend fuels. Oxygenate-containing fuels are described in ASTM D-4814-91.

Methanol and ethanol are commonly used oxygenates. They are primarily used as fuels. Other oxygenates, such as ethers, for example methyl-t-butyl ether, are more often used as octane number enhancers for gasoline.

Mixtures of fuels are useful. Examples of fuel mixtures are combinations of gasoline and ethanol, diesel fuel and ether, gasoline and nitromethane, etc.

Particularly preferred fuels are gasoline, that is, a mixture of hydrocarbons having an ASTM boiling point of 60° C. at the 10% distillation point to about 205° C. at the 90% distillation point, oxygenates, and gasoline-oxygenate blends, all as defined in the aforementioned ASTM Specifications for automotive gasolines. Most preferred is gasoline.

The fuel compositions of the present invention may contain other additives which are well known to those of skill in the art. These can include anti-knock agents such as tetra-alkyl lead compounds, lead scavengers such as haloakanes, dyes, antioxidants such as hindered phenols, rust inhibitors such as alkylated succinic acids and anhydrides and derivatives thereof, bacteriostatic agents, auxiliary dispersants and detergents, gum inhibitors, fluidizers, metal deactivators, demulsifiers, anti-icing agents and the like. The fuel compositions of this invention may be lead-containing or lead-free fuels. Preferred are lead-free fuels.

The products of this invention provide a number of benefits to a treated fuel, including detergency, anticorrosion and the like.

In one particular embodiment of this invention, the motor fuel compositions contain an amount of additives sufficient to provide total intake system cleanliness. In another embodiment, they are used in amounts sufficient to prevent or reduce the formation of intake valve deposits or to remove them where they have formed.

As mentioned hereinabove, fluidizers may be used in the fuel compositions of the instant invention. Useful fluidizers include natural oils or synthetic oils, or mixtures thereof. Natural oils include mineral oils, vegetable oils, animal oils, and oils derived from coal or shale. Synthetic oils include hydrocarbon oils such as alkylated aromatic oils, olefin oligomers, esters, including esters of polycarboxylic acids, polyols, polyethers, poly(oxyalkylene)glycols, alkylphenol-derived polyethers, and others.

Fluidizers are usually fuel soluble, meaning they are soluble in the fuel in amounts of at least 0.1% by weight, more preferably at least 1% by weight. Certain fluidizers, for example, butylene- and propylene oxide derived fluidizers, are generally soluble in fuels at all levels. These are readily prepared from alcohol, glycol and phenol initiators under superatmospheric conditions, preferably in the presence of basic catalysts.

Especially preferred mineral oils are paraffinic oils containing no more than about 20% unsaturation, that is, no more than 20% of the carbon to carbon bonds are olefinic.

Specific examples of synthetic oil fluidizers are polyoxyalkylene mono- and polyols, ether derivatives thereof and N-vinylpyrrolidinone addition products thereof, polyalphaolefins, and hydrogenated polyalphaolefins.

Particularly useful synthetic oils are the polyether oils such as those marketed under the UCON tradename by Union Carbide Corporation, poly(oxyalkylene)glycols such as those marketed under the EMKAROX tradename by ICI Chemicals and described in EP 0647700-A1 based on U.S. Ser. No. 133442 filed Oct. 6, 1993 and polyester oils derived from a polyol and one or more monocarboxylic acids such as those marketed by Hatco Corporation.

Other examples are polyoxyalkylene compounds prepared from $C_{1-30}$ alcohols or $C_{7-24}$ alkylphenols and sufficient propylene- or butylene oxide such that molecular weight ranges from about 200 to about 5,000, and monoethers and N-vinylpyrrolidinone addition products thereof. Additional fluidizers include polyoxyalkylene compounds prepared from glycols or polyols having from 2 to about 10 carbon atoms and sufficient propylene- or butylene oxide such that overall molecular weight ranges from about 200 to about 6,000 and ether derivatives thereof.

Preferably, the fluidizers have a kinematic viscosity ranging from about 2 to about 25 centistokes at 100° C., preferably from about 4 to about 20 centistokes, and often up to about 15 centistokes. If the viscosity of the fluidizer is too high, a problem that may arise is the development of octane requirement increase (ORI) wherein the octane value demands of the engine tend to increase with time of operation.

While both mineral oils and synthetic oils are generally useful as fluidizers over the entire preferred viscosity range, it has been observed that at the lower end of the viscosity range, synthetic oils tend to provide somewhat superior performance compared to mineral oils.

It has been found that fluidizers, particularly when used within the ranges specified herein, together with the compositions of this invention, improve detergency and emissions, and reduce the tendency toward valve sticking. Amounts of the various additives, including individual amounts to be used in the fuel composition, and relative amounts of additives are given hereinafter.

The fuel compositions of this invention may contain auxiliary dispersants. A wide variety of dispersants are known in the art and may be used together with the amide compounds described herein. Preferred auxiliary dispersants are Mannich type dispersants, acylated nitrogen-containing dispersants, aminophenol dispersants, aminocarbamate dispersants, ester dispersants and amine dispersants.

Acylated nitrogen-containing compounds include reaction products of hydrocarbyl-substituted carboxylic acylating agents such as substituted carboxylic acids or derivatives thereof with ammonia or amines. Especially preferred are succinimide dispersants.

Acylated nitrogen-containing compounds are known in the art and are disclosed in, for example, U.S. Pat. Nos. 4,234,435; 3,215,707; 3,219,666; 3,231,587 and 3,172,892, which are hereby incorporated by reference for their disclosures of the compounds and the methods of preparation.

The auxiliary dispersant may also be an ester. These compounds are prepared by reacting a hydrocarbyl-substituted carboxylic acylating agent with at least one organic hydroxy compound. In another embodiment, the ester dispersant is prepared by reacting the acylating agent with a hydroxyamine. Preferred are succinic esters.

Carboxylic esters and methods of making the same are known in the art and are disclosed in U.S. Pat. Nos. 3,219,666, 3,381,022, 3,522,179 and 4,234,435 which are hereby incorporated by reference for their disclosures of the preparation of carboxylic ester dispersants.

The carboxylic esters may be further reacted with at least one amine and preferably at least one polyamine. These nitrogen-containing carboxylic ester dispersant compositions are known in the art, and the preparation of a number of these derivatives is described in, for example, U.S. Pat. Nos. 3,957,854 and 4,234,435 which have been incorporated by reference previously.

Also included among the auxiliary dispersants are Mannich type dispersants. Mannich products are formed by the reaction of at least one aldehyde, at least one amine having at least one N—H group and at least one hydroxyaromatic compound.

Mannich products are described in the following patents: U.S. Pat. No. 3,980,569; U.S. Pat. No. 3,877,899; and U.S. Pat. No. 4,454,059 (herein incorporated by reference for their disclosure to Mannich products).

The auxiliary dispersant may be a polyalkene-substituted amine. Polyalkene-substituted amines are well known to those skilled in the art. Typically, polyalkene-substituted amines are prepared by reacting olefins and olefin polymers (polyalkenes) and halogenated derivatives thereof with amines (mono- or polyamines). These amines are disclosed in U.S. Pat. Nos. 3,275,554; 3,438,757; 3,454,555; 3,565,804; 3,755,433; and 3,822,289. These patents are hereby incorporated by reference for their disclosure of hydrocarbyl amines and methods of making the same.

Aminophenols are also included among useful auxiliary dispersants that may be used in the fuel composition of this invention. Typically, such materials are prepared by reducing hydrocarbyl substituted nitrophenols to the corresponding aminophenol. Useful aminophenols include those described in Lange, U.S. Pat. Nos. 4,320,000 and 4,320,021. Aminophenols and methods for preparing are described in U.S. Pat. Nos. 4,100,082 and 4,200,545 to Clason et al, U.S. Pat. No. 4,379,065 (Lange) and U.S. Pat. No. 4,425,138 (Davis). It should be noted that the term "phenol" used in the context of aminophenols is not intended to limit the compounds referred to in that manner as being only hydroxybenzene derivatives. The term "phenol" is intended to encompass hydroxy aromatic compounds, including hydroxybenzene compounds, naphthols, catechols and others as described in the foregoing patents, all of which are incorporated herein by reference for relevant disclosures contained therein.

Also included among useful auxiliary dispersants are aminocarbamate dispersants such as those described in U.S. Pat. No. 4,288,612, which is incorporated herein by reference for relevant disclosures contained therein.

Treating levels of the additives used in this invention are often described in terms of pounds of additive per thousand barrels (PTB) of fuel. PTB values may be converted to approximate values expressed as parts (by weight) per million parts (by weight) of fuel by multiplying PTB by 4 for gasoline and by 3.3 for diesel oil and fuel oil. To determine precise values it is necessary that the specific gravity of the fuel is known. The skilled person can readily perform the necessary mathematical calculations.

The fuel compositions of this invention contain from about 5 to about 500 pounds per thousand barrels (PTB) of fuel additive, preferably from about 10 to about 250 PTB, more preferably from about 20 to about 100 PTB.

Fluidizers, when used, are generally present in amounts ranging from about 1 to about 500 PTB, more often from about 10 to about 250 PTB and most preferably from about 10 to about 150 PTB.

Relative amounts by weight, of the nitrogen-containing compound to fluidizer oil typically range from about 1:0 that is, essentially free of fluidizer, up to 1:10, more often from about 1:0.5–2:0, preferably from about 1:0.75–1.25.

Additive Concentrates

As mentioned hereinabove, the additives for use in fuels may be supplied as additive concentrates which are then diluted with normally liquid fuels.

The following Table illustrates additive concentrates for use in fuels.

|  | Concentrate (% by Weight) | |
| --- | --- | --- |
| Component | F-I | F-II |
| Alkylated aromatic hydrocarbon[1] | 15.76 | 19.2 |
| Product of Example 12-B | 34 | 38 |
| Demulsifiers | 0.22 | |
| Polyether Oil[2] | | 42.8 |
| Mineral oil | 45.94 | |
| 2-Ethylhexanol | 4.54 | |

[1]= HISOL-10, Ashland Chemical Co.
[2]= EMKAROX AF-20, ICI

The following examples illustrate several fuel compositions of this invention. When referring to compounds described in the Examples, amounts are given in parts and percentages by weight as prepared. Unless indicated otherwise, all other parts and percentages are by weight and amounts of additives are expressed in amounts substantially free of mineral oil or hydrocarbon solvent diluent. The abbreviation 'PTB' means pounds of additive per thousand barrels of fuel.

The following Table illustrates several fuel compositions of the instant invention comprising unleaded gasoline and the indicated amounts of additive in percent by weight concentrate in fuel.

| UNLEADED GASOLINE + % WEIGHT ADDITIVE CONCENTRATE | | |
| --- | --- | --- |
| Concentrate | F-A | F-B |
| F-I | 0.08 | |
| F-II | | 0.07 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications that fall within the scope of the appended claims.

What is claimed is:

1. A process comprising reacting, optionally in the presence of an acidic catalyst selected from the group consisting of organic sulfonic acids, heteropolyacids, Lewis acids, and mineral acids, (A) at least one olefinic compound containing at least one group of the formula:

and (B) at least one carboxylic reactant selected from the group consisting of compounds of the formula

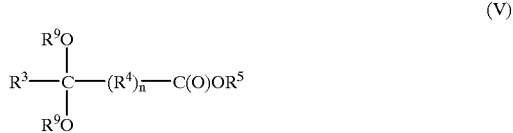

wherein $R^3$ is H or an aliphatic group, $R^5$ and $R^9$ are independently lower alkyl;

$R^4$ is a divalent hydrocarbylene group, and n is 0 or 1, in amounts ranging from 0.6 moles (B) per mole of (A) to 3 moles (B) per equivalent of (A).

2. The process of claim 1 wherein the product formed from reaction of (A) and (B) is further reacted with from about 0.5 equivalents up to about 2 moles, per mole of (B) of at least one of (C) ammonia or a hydrazine or an amine characterized by the presence within its structure of at least one H—N group.

3. The process of claim 1 wherein the product formed from reaction of (A) and (B) is further reacted with from about 0.5 equivalents up to about 2 moles of (B) of at least one reactive metal or reactive metal compound.

4. The process of claim 1 wherein the at least one reactant (B) is at least one compound of the formula

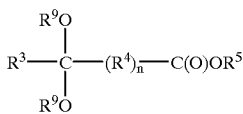
(IV)

wherein $R^3$ is H and $R^5$ and $R^9$ are lower alkyl groups selected from the group consisting of methyl, ethyl, propyl and butyl and n=0, and the olefinic compound (A) has the general formula

(III)

wherein each of $R^1$ and $R^2$ is, independently, hydrogen or a hydrocarbon based group and each of $R^6$, $R^7$ and $R^8$ is, independently, hydrogen or a hydrocarbon based group.

5. The process of claim 4 wherein each of $R^1$ and $R^2$ is hydrogen and $R^6$ is H or a lower alkyl group and the group $(CH(R^7)(R^8))$ is a hydrocarbyl group containing from 7 to about 5000 carbon atoms.

6. The process of claim 5 wherein the group $(CH(R^7)(R^8))$ is an aliphatic group containing from about 30 to about 200 carbon atoms and the olefinic compound is derived from homopolymerized and interpolymerized $C_{2-18}$ olefins, wherein the olefinic compound has $\overline{M}_n$ ranging from about 200 to about 7,000.

7. The process of claim 4 wherein the olefinic compound is a polyolefin comprising a mixture of isomers, at least about 50% by weight of the mixture comprising isomers of the formula

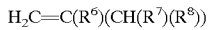

wherein $R^6$ is H or lower alkyl.

8. The process of claim 6 wherein the polyolefin is a polybutene and $R^6$ is methyl.

9. The process of claim 4 wherein the olefinic compound is a polyolefin comprising a mixture of isomers wherein from about 50% to 65% are trisubstituted olefins wherein one substituent contains from 2 to about 5000 carbon atoms and the other two substituents are lower alkyl.

10. The process of claim 1 wherein the olefinic compound is selected from the group consisting of a linear $\alpha$-olefin containing from 8 to about 28 carbon atoms, an ethylene-alpha-olefin copolymer, and an ethylene-alpha olefin-diene terpolymer.

11. The process of claim 2 wherein (C) is selected from the group consisting of an alkylene polyamine, an alkylene polyamine bottoms product, and a condensed polyamine derived from at least one hydroxy-containing material and at least one alkylene polyamine or alkylene polyamine bottoms product.

12. A composition prepared by the process of claim 1.

13. A composition prepared by the process of claim 2.

14. An additive concentrate for formulating lubricating oil or fuel compositions comprising from about 20% to about 99% by weight of a normally liquid, substantially inert organic diluent and from about 10% to about 80% by weight of the composition described in claim 13.

15. A lubricating composition comprising a major amount of an oil of lubricating viscosity and a minor amount of the composition described in claim 13.

* * * * *